(12) United States Patent
Meng

(10) Patent No.: US 12,257,068 B2
(45) Date of Patent: Mar. 25, 2025

(54) SLEEP MONITORING METHOD AND APPARATUS, SLEEP AID DEVICE AND METHOD

(71) Applicants: Beijing BOE Health Technology Co., Ltd., Beijing (CN); BOE TECHNOLOGY GROUP CO., LTD., Beijing (CN)

(72) Inventor: Guifang Meng, Beijing (CN)

(73) Assignees: BEIJING BOE HEALTH TECHNOLOGY CO., LTD., Beijing (CN); BOE TECHNOLOGY GROUP CO., LTD., Beijing (CN)

( * ) Notice: Subject to any disclaimer, the term of this patent is extended or adjusted under 35 U.S.C. 154(b) by 445 days.

(21) Appl. No.: 17/638,816

(22) PCT Filed: Apr. 12, 2021

(86) PCT No.: PCT/CN2021/086662
§ 371 (c)(1),
(2) Date: Feb. 26, 2022

(87) PCT Pub. No.: WO2021/238457
PCT Pub. Date: Dec. 2, 2021

(65) Prior Publication Data
US 2022/0304623 A1     Sep. 29, 2022

(30) Foreign Application Priority Data

May 29, 2020   (CN) .......................... 202010474787.0

(51) Int. Cl.
*A61B 5/00*     (2006.01)
*A61B 5/16*     (2006.01)
*A61B 5/369*    (2021.01)

(52) U.S. Cl.
CPC ............ *A61B 5/4815* (2013.01); *A61B 5/165* (2013.01); *A61B 5/369* (2021.01); *A61B 5/4809* (2013.01);
(Continued)

(58) Field of Classification Search
None
See application file for complete search history.

(56) References Cited

U.S. PATENT DOCUMENTS

2002/0193151 A1* 12/2002 Edreich ................... H04M 1/05
                                                         455/74
2016/0262704 A1    9/2016 Min et al.
(Continued)

FOREIGN PATENT DOCUMENTS

AU     2019285065 A1     1/2021
CA        3103463 A1    12/2019
(Continued)

OTHER PUBLICATIONS

International Search Report and Written Opinion for International Application No. PCT/CN2021/086662 mailed Jul. 12, 2021.
(Continued)

*Primary Examiner* — William J Levicky
*Assistant Examiner* — Willow Grace Welch
(74) *Attorney, Agent, or Firm* — Perilla Knox & Hildebrandt LLP; Kenneth A. Knox

(57) ABSTRACT

A sleep testing method, a sleep testing apparatus, a sleep-aiding device, and a sleep-aiding method are described. The sleep testing method comprises: acquiring an electroencephalogram signal of a user; processing the electroencephalogram signal to obtain energy values of the electroencephalogram signal in a plurality of set frequency bands; calculating a relative energy value of the electroencephalogram signal in the plurality of set frequency bands; and
(Continued)

determining a sleep state, mental stress and the degree of fatigue according to the relative energy value. According to the sleep testing method, the sleep state, the mental stress, and the degree of fatigue of a user can be simultaneously determined just according to an electroencephalogram signal, and a plurality of pieces of testing data related to sleep can be obtained in a single instance of testing.

17 Claims, 2 Drawing Sheets

(52) U.S. Cl.
CPC .......... *A61B 5/4812* (2013.01); *A61B 5/6814* (2013.01); *A61M 2230/005* (2013.01)

(56) References Cited

U.S. PATENT DOCUMENTS

| | | | | |
|---|---|---|---|---|
| 2019/0053766 | A1* | 2/2019 | Mijovic | A61B 5/378 |
| 2019/0381071 | A1 | 12/2019 | Zasloff et al. | |
| 2020/0261689 | A1* | 8/2020 | Harrison | A61B 5/6831 |
| 2021/0178112 | A1* | 6/2021 | Ning | G16H 20/30 |

FOREIGN PATENT DOCUMENTS

| | | | |
|---|---|---|---|
| CN | 101596101 | A | 12/2009 |
| CN | 101596101 | B | 3/2011 |
| CN | 102247122 | A | 11/2011 |
| CN | 102274022 | A | 12/2011 |
| CN | 102302365 | A | 1/2012 |
| CN | 102274022 | B | 2/2013 |
| CN | 103989485 | A | 8/2014 |
| CN | 204506763 | U | 7/2015 |
| CN | 104997522 | A | 10/2015 |
| CN | 105160812 | A | 12/2015 |
| CN | 204838733 | U | 12/2015 |
| CN | 105476631 | A | 4/2016 |
| CN | 105942974 | A | 9/2016 |
| CN | 106388818 | A | 2/2017 |
| CN | 107126615 | A | 9/2017 |
| CN | 107343786 | A * | 11/2017 |
| CN | 108211081 | A | 6/2018 |
| CN | 109222961 | A | 1/2019 |
| CN | 109276232 | A | 1/2019 |
| CN | 109363669 | A | 2/2019 |
| CN | 109363670 | A | 2/2019 |
| CN | 109464130 | A | 3/2019 |
| CN | 109925120 | A | 6/2019 |
| CN | 109999314 | A | 7/2019 |
| CN | 110251801 | A | 9/2019 |
| CN | 209450771 | U | 10/2019 |
| CN | 109999314 | B | 8/2020 |
| CN | 111528839 | A | 8/2020 |
| WO | 2019241503 | A1 | 12/2019 |

OTHER PUBLICATIONS

1st Office Action for CN Patent Application No. 202010474787.0 mailed Oct. 25, 2022.

Xueli Shen, "Research on Scalp EEG Feature Extraction and Recognition based on Time-Frequency Analysis," Dec. 2011.

Tang, W.; Chen, S.; Xiao, Y.; Jiang, G.; Tian, Z, "Study on Mental Workload in Manipulator Teleoperation Mission," Manned Spacefl. 2017, 23, 688-696.

Zhu Y.; Zeng Y.; Feng Z.; et al., "The Detection Method for Driving Fatigue based on EEG Signals," J. Changchun Univ. Sci. Technol. (Nat. Sci. Ed.) (2016) 39(05), 119-122.

Zhou Hui, "The Research of EEG Characteristics of Sleep with Photic Stimulation," Nanking Univ. of Aero. and Astronautics. (Jan. 2015).

* cited by examiner

SLEEP MONITORING METHOD AND APPARATUS, SLEEP AID DEVICE AND METHOD

CROSS REFERENCE TO RELATED APPLICATION

The present disclosure is a national phase application under 35 U.S.C. § 371 of International Application No. PCT/CN2021/086662 filed Apr. 12, 2021, which claims the benefit of and priority to Chinese Patent Application No. 202010474787.0, filed on May 29, 2020, entitled by "Sleep Monitoring Method and APPARATUS, Sleep Aid Device and Method," where the contents of both of which are incorporated by reference in their entireties herein.

TECHNICAL FIELD

The present disclosure relates to the technical field of sleep aiding and assistance and, in particular, to a sleep monitoring method, a sleep monitoring apparatus, a sleep aid device, and a sleep aid method.

BACKGROUND

With the accelerated pace of life, the quality of sleep among young people is very poor, and high-quality sleep has a great impact on human health. At present, there is no sleep monitoring method and apparatus capable of simultaneously monitoring a sleep state, stress index, and fatigue index. An existing sleep aid device does not monitor the sleep state, and cannot perform sleep aid in a targeted way to improve sleep quality.

Therefore, it is necessary to provide a sleep monitoring method, a sleep monitoring apparatus, a sleep aid device, and a sleep aid method.

BRIEF SUMMARY

According to an aspect of the present disclosure, there is provided a sleep monitoring method, comprising: acquiring the user's EEG signal; processing the EEG signal to obtain energy values of the EEG signal in a plurality of set frequency bands; calculating relative energy values of the EEG signal in the plurality of set frequency bands; and determining sleep state, mental stress, and fatigue level according to the relative energy values.

In an exemplary embodiment of the present disclosure, the plurality of set frequency bands include a first frequency band, a second frequency band, a third frequency band, and a fourth frequency band. The first frequency band is greater than or equal to 0.5 Hz and less than 4 Hz. The second frequency band is greater than or equal to 4 Hz and less than 8 Hz. The third frequency band is greater than or equal to 8 Hz and less than 12 Hz. The fourth frequency band is greater than or equal to 12 Hz and less than or equal to 30 Hz.

In an exemplary embodiment of the present disclosure, the calculating the relative energy values of the EEG signal in the plurality of set frequency bands includes: calculating the sum of the energy values of the EEG signal; and determining each of the relative energy values as the ratio of the energy value of the EEG signal in a respective set frequency band to the sum.

In an exemplary embodiment of the present disclosure, the determining the sleep state according to the relative energy values includes:
calculating a sleep index SI by the following formulas:

$$SI=(K1*E1+K2*E2)/(K3*E3+K4*E4),$$

$$K1+K2=1,$$

$$K3+K4=1,$$

where, the value range of K1 is 0.3-0.5, the value range of K3 is 0.7-1, E1 is the relative energy value of the EEG signal in the first frequency band, E2 is the relative energy value of the EEG signal in the second frequency band, E3 is the relative energy value of the EEG signal in the third frequency band, and E4 is the relative energy value of the EEG signal in the fourth frequency band; and calculating a deep sleep index DI by the following formula:

$$DI=E1/E2.$$

If SI<TH1, it is determined to be an awake period. If SI≥TH1 and DI<TH2, it is determined to be a light sleep period. If SI≥TH1 and DI≥TH2, it is determined to be a deep sleep period. Besides, in the above formulas, TH1 is a constant whose value range is 1.5-4, and TH2 is a constant whose value range is 0.8-2.

In an exemplary embodiment of the present disclosure, the determining the mental stress according to the relative energy values includes: calculating a pressure index S according to the following formula:

$$S=E2/(E3+E4),$$

where, the larger the stress index, the higher the mental stress.

In an exemplary embodiment of the present disclosure, the determining the fatigue level according to the relative energy values includes: calculating a fatigue index F according to the following formula:

$$F=(E1+E2)/E4,$$

where, the larger the fatigue index, the deeper the degree of fatigue.

According to an aspect of the present disclosure, there is provided a sleep monitoring apparatus, comprising: a signal acquisition sub-circuit, configured to acquire the user's EEG signal; a first processing sub-circuit, configured to process the EEG signal to obtain energy values of the EEG signal in a plurality of set frequency bands; a second processing sub-circuit, configured to calculate relative energy values of the EEG signal in the plurality of set frequency bands; and a state determination sub-circuit configured to determine sleep state, mental stress, and fatigue level according to the relative energy values.

According to an aspect of the present disclosure, there is provided a sleep aid device, comprising: a wearable sleep aid; an electrode sheet, arranged on the wearable sleep aid and configured to be attached to the user's head; a processor, electrically connected to the electrode sheet, and configured to receive the EEG signal acquired by the electrode sheet, thereby implementing the sleep monitoring method described in any one of the above, and controlling the output device according to the sleep state; and an output device, electrically connected to the processor and configured to operate according to the control signal output by the processor.

In an exemplary embodiment of the present disclosure, the wearable sleep aid includes one or both of an eye mask and a U-shaped pillow.

In an exemplary embodiment of the present disclosure, the wearable sleep aid further includes: a temperature sensor, electrically connected to the input end of the processor, and configured to monitor the ambient temperature.

In an exemplary embodiment of the present disclosure, the output device includes one or more of a heater, a music player, a signal transmitter, and a display screen. The control end of the heater is electrically connected to the output end of the processor. The control end of the music player is electrically connected to the output end of the processor. The signal transmitter is electrically connected to the output end of the processor. The input end of the display screen is electrically connected to the output end of the processor.

In an exemplary embodiment of the present disclosure, the music player is an earphone or a speaker.

In an exemplary embodiment of the present disclosure, the connection wire of the earphone is retractable.

According to an aspect of the present disclosure, there is provided a sleep aid method, which is applicable to the sleep aid device described in any of the above. The sleep aid method includes: monitoring the sleep state according to the sleep monitoring method described in any one of the above; and controlling the output device according to the sleep state.

In an exemplary embodiment of the present disclosure, the controlling the output device according to the sleep state includes: when it is detected that the user enters a light sleep period, the volume of the music player is controlled to decrease; and when it is detected that the user enters a deep sleep period, the music player is controlled to stop playing music.

In an exemplary embodiment of the present disclosure, the controlling the output device according to the sleep state includes: when it is detected that the user enters a light sleep period, the heating temperature of the heater is controlled to gradually decrease; and when it is detected that the user enters a deep sleep period, the heater is controlled to stop heating.

BRIEF DESCRIPTION OF THE DRAWINGS

The accompanying drawings, which are incorporated in and constitute a part of the present specification, illustrate embodiments consistent with the present disclosure and together with the description serve to explain the principle of the present disclosure. Understandably, the drawings in the following description are only some embodiments of the present disclosure, and for those of ordinary skill in the art, other drawings can also be obtained from these drawings without creative effort.

DETAILED DESCRIPTION

Figure 1:
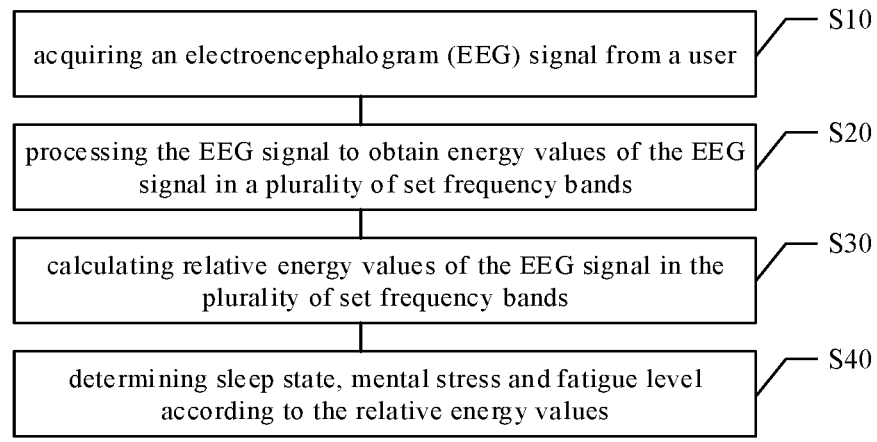
FIG. 1 schematically shows a flowchart of the sleep monitoring method according to an exemplary implementation of the present invention.

Example embodiments will now be described more fully with reference to the accompanying drawings. Example embodiments, however, may be embodied in various forms and should not be construed as limited to the examples set forth herein. Rather, these embodiments are provided so that the present disclosure will be thorough and complete, and will fully convey the concept of example embodiments to those skilled in the art. The described features, structures, or characteristics may be combined in any suitable way in one or more embodiments. In the following description, numerous specific details are provided in order to give a thorough understanding of embodiments of the present disclosure. However, those skilled in the art will appreciate that the technical solutions of the present disclosure may be practiced without one or more of the specific details, or other methods, components, devices, steps, etc. may be adopted. In other instances, well-known solutions have not been shown or described in detail to avoid obscuring aspects of the present disclosure.

Furthermore, the drawings are merely schematic illustrations of the present disclosure and are not necessarily drawn to scale. The same reference numerals in the drawings denote the same or similar parts, and thus their repeated descriptions will be omitted. Some of the block diagrams shown in the figures are functional entities that do not necessarily correspond to physically or logically separate entities. These functional entities may be implemented in software, or in one or more hardware modules or integrated circuits, or in different networks and/or processor devices and/or microcontroller devices.

An exemplary embodiment first provides a sleep monitoring method. Referring to FIG. 1, the sleep monitoring method may include the following steps.

In Step S10, the EEG signal of the user is acquired.

In Step S20, the EEG signal is processed to obtain energy values of the EEG signal in a plurality of set frequency bands.

In Step S30, relative energy values of the EEG signal in the plurality of set frequency bands are calculated.

In Step S40, each of sleep state, mental stress, and fatigue level is determined according to the relative energy values.

According to the sleep monitoring method of an exemplary embodiment, on one hand, the user's sleep state, mental stress, and fatigue level may be determined simultaneously only based on the EEG signal, and multiple sleep-related monitoring data may be obtained through a single monitoring. On the other hand, the device required by this method is relatively simple, which is convenient for use in a portable sleep aid device.

Next, the sleep monitoring method in an exemplary embodiment will be further described.

In Step S10, the EEG signal of the user is acquired.

In an example embodiment, the EEG signal may include a left EEG signal and a right EEG signal. EEG signal is a non-stationary random signal. Simultaneous monitoring of the left and right EEG signals makes subsequent monitoring results more accurate.

In Step S20, the EEG signal is processed to obtain energy values of the EEG signal in a plurality of set frequency bands.

In an example embodiment, the plurality of set frequency bands include a first frequency band, a second frequency band, a third frequency band and a fourth frequency band. The first frequency band is greater than or equal to 0.5 Hz and less than 4 Hz. The second frequency band is greater than or equal to 4 Hz and less than 8 Hz. The third frequency band is greater than or equal to 8 Hz and less than 12 Hz. The fourth frequency band is greater than or equal to 12 Hz and less than or equal to 30 Hz.

The method for processing the EEG signal may be wavelet packet decomposition, wavelet transform, Fourier transform, etc., and the above methods are all known in the art, and therefore will not be repeated here.

In Step S30, relative energy values of the EEG signal in the plurality of set frequency bands are calculated.

In an example embodiment, the sum of the energy values of the EEG signal may be calculated first. The sum E of the energy values of the EEG signal may be calculated by the following formula:

$$E = E1L + E2L + E3L + E4L + E1R + E2R + E3R + E4R,$$

where, E1L is the energy value of the left EEG signal in the first frequency band, E2L is the energy value of the left EEG signal in the second frequency band, E3L is the energy value of the left EEG signal in the third frequency band, and E4L is the energy value of the left EEG signal in the fourth frequency band, E1R is the energy value of the right EEG signal in the first frequency band, E2R is the energy value of the right EEG signal in the second frequency band, E3R is the energy value of the right EEG signal in the third frequency band, and E4R is the energy value of the right EEG signal in the fourth frequency band.

Then, the ratio of the energy value of the EEG signal in each set frequency band to the sum is calculated as the respective relative energy value.

Specifically, they are as follows:

$$E1 = (E1L + E1R)/E,$$

$$E2 = (E2L + E2R)/E,$$

$$E3 = (E3L + E3R)/E,$$

$$E4 = (E4L + E4R)/E,$$

where, E1 is the relative energy value of the EEG signal in the first frequency band, E2 is the relative energy value of the EEG signal in the second frequency band, E3 is the relative energy value of the EEG signal in the third frequency band, and E4 is the relative energy value of the EEG signal in the fourth frequency band.

In Step S40, sleep state, mental stress and fatigue level is determined according to the relative energy values.

In an example embodiment, the sleep index SI may be calculated by the following formulas:

$$SI = (K1*E1 + K2*E2)/(K3*E3 + K4*E4),$$

$$K1 + K2 = 1,$$

$$K3 + K4 = 1,$$

where, the value range of K1 is 0.3-0.5, and the value range of K3 is 0.7-1. In some embodiments, K1=0.4, K2=0.6, K3=0.8, and K4=0.2.

The deep sleep index DI may be calculated by the following formula:

$$DI = E1/E2.$$

If SI<TH1, it is determined to be an awake period. If SI≥TH1 and DI<TH2, it is determined to be a light sleep period. If SI ≥TH1 and DI≥TH2, it is determined to be a deep sleep period. In the formula, TH1 is a constant whose value range is 1.5-4, and TH2 is a constant whose value range is 0.8-2.

The pressure index S may be calculated according to the following formula:

$$S = E2/(E3 + E4).$$

The larger the stress index, the higher the mental stress. The mild stress threshold, moderate stress threshold, and severe stress threshold may be also set. The stress index greater than or equal to the mild stress threshold indicates that the user is under mild stress. The stress index greater than or equal to the moderate stress threshold indicates that the user is under greater mental stress. The index greater than or equal to the severe stress threshold indicates that the user is under high mental stress.

The fatigue index F may be calculated according to the following formula:

$$F = (E1 + E2)/E4,$$

The larger the fatigue index, the deeper the fatigue degree. The mild fatigue threshold, moderate fatigue threshold, and severe fatigue threshold may be also set. The fatigue index greater than or equal to the mild fatigue threshold indicates that the user is less fatigued. The fatigue index greater than or equal to the moderate fatigue threshold indicates that the user is more fatigued. The fatigue index greater than or equal to the severe fatigue threshold indicates that the user is deeply fatigued.

Additionally, although the various steps of methods of the present disclosure are depicted in the figures in a particular order, this does not require or imply that the steps must be performed in the particular order or that all illustrated steps must be performed to achieve the desired result. Additionally or alternatively, certain steps may be omitted, multiple steps may be combined into one step for execution, and/or one step may be decomposed into multiple steps for execution, and the like.

Figure 2:
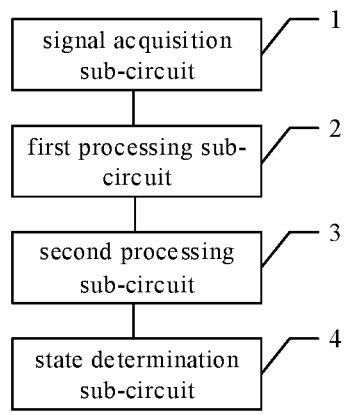
FIG. 2 schematically shows a structural block diagram of the sleep monitoring apparatus according to an exemplary embodiment of the present invention.

Further, an exemplary embodiment of the present disclosure further provides a sleep monitoring apparatus corresponding to the above-mentioned sleep monitoring method. Referring to FIG. 2, the sleep monitoring apparatus may include a signal acquisition sub-circuit 1, a first processing sub-circuit 2, a second processing sub-circuit 3, and a state determination sub-circuit 4. The signal acquisition sub-circuit 1 may be used to acquire the user's EEG signal. The first processing sub-circuit 2 may be used to process the EEG signal to obtain energy values of the EEG signal in a plurality of set frequency bands. The second processing sub-circuit 3 may be used to calculate the relative energy values of the EEG signal in the plurality of set frequency bands. The state determination sub-circuit 4 may be used to calculate determine sleep status, mental stress, and fatigue levels according to the relative energy values. The processor 8 may include the above-mentioned signal acquisition sub-circuit 1, first processing sub-circuit 2, second processing sub-circuit 3 and state determination sub-circuit 4. The processor 8 may be hardware such as a single-chip microcomputer, a microprocessor, a CPU, etc. with data processing functions. The first processing sub-circuit 2, the second processing sub-circuit 3, and the state determination sub-circuit 4 may be implemented by a single circuit structure, or may be implemented by multiple circuit structures respectively.

The specific details of each sub-circuit in the above-mentioned sleep monitoring apparatus have been described in detail in the corresponding sleep monitoring method, and therefore are not repeated here.

It should be noted that although several modules or sub-circuits of the apparatus for action performance are mentioned in the above detailed description, this division is not mandatory. Indeed, according to embodiments of the present disclosure, features and functions of two or more modules or sub-circuits described above may be embodied in one module or sub-circuit. Conversely, features and functions of one module or sub-circuit described above may be further divided and embodied into multiple modules or sub-circuits.

Currently, work pressure is high, and many people need to take a break at noon to replenish their physical strength and better work in the afternoon. Some people travel more and need to supplement sleep in cars, trains, or planes. Some people work overtime for a long time, and need to take a nap in the office. Therefore, some eye masks, U-shaped pillows, etc. are needed to create a sleeping atmosphere and provide a comfortable posture for users. However, the existing eye masks and U-shaped pillows are all have single function, and it is impossible to know the sleep state, mental stress, and fatigue level of the user.

Figure 3:
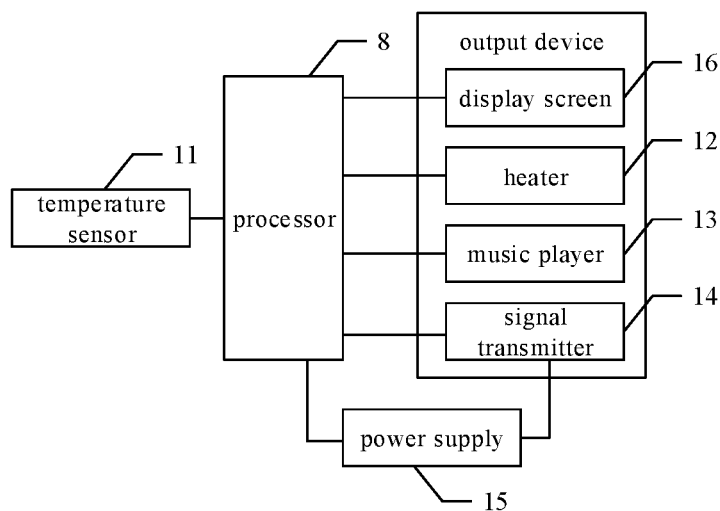
FIG. 3 schematically shows a structural block diagram of the sleep aid device according to an exemplary embodiment of the present invention.
Figure 4:
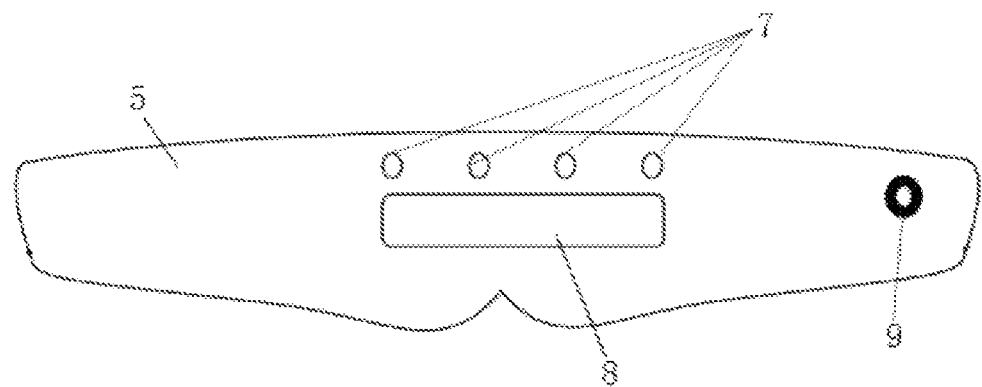
FIG. 4 schematically shows a structural diagram of the sleep aid device according to an exemplary embodiment of the present invention.
Figure 5:
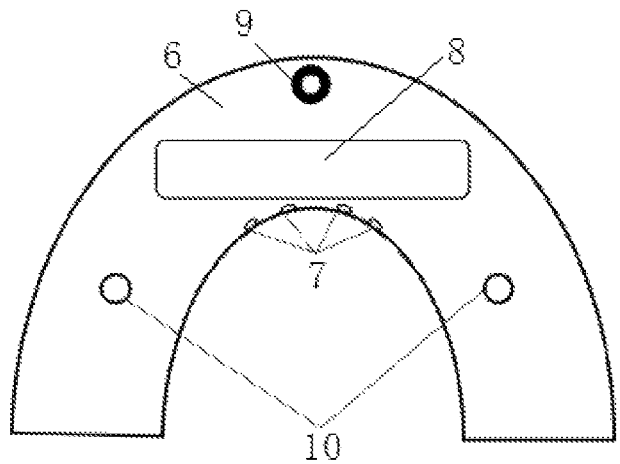
FIG. 5 schematically shows a structure diagram of the sleep aid device according to another exemplary embodiment of the present invention.

Further, an exemplary embodiment of the present disclosure further provides a sleep aid device. Referring to FIG. 3, FIG. 4, and FIG. 5, the sleep aid device may include a wearable sleep aid, an electrode sheet 7, a processor 8 and an output device. The electrode sheet 7 is arranged on the wearable sleep aid and can be attached to the user's head. The processor 8 is electrically connected to the electrode sheet 7 for receiving the EEG signal acquired by the electrode sheet 7, thus implementing the above-mentioned sleep monitoring method, and controlling the output device according to the sleep state. The output device is electrically connected to the processor, and is configured to operate according to the control signal output by the processor. The processor 8 may be hardware with a data processing function, such as a single-chip microcomputer, a microprocessor, and a CPU.

In an exemplary embodiment, as shown in FIG. 4, the wearable sleep aid may include an eye mask 5. The outer cover of the eye mask 5 is a soft cloth, and the outer cover is filled with soft fillers. In addition, in some other example embodiments, as shown in FIG. 5, the wearable sleep aid may include a U-shaped pillow 6. The U-shaped pillow 6 includes a cover made of soft cloth, and the cover is filled with filling materials such as memory foam. The outer cover may be disassembled for cleaning the outer cover, which is convenient to use, clean and hygienic, and helps to protect the internal circuits.

In an exemplary embodiment, the electrode sheet 7 is a flexible EEG electrode sheet, and the electrode sheet 7 may be a metal electrode such as silver/silver chloride. A total of four electrode sheets 7 are arranged, including left frontal EEG electrode sheet, right frontal EEG electrode sheet, reference electrode sheet and ground electrode sheet, so as to obtain left frontal EEG signal and right frontal EEG signal. Four openings are provided in the outer cover, and four electrode sheets 7 are correspondingly arranged at the four openings. Thus, the electrode sheets 7 may fit the skin of the user's head to the greatest extent and the comfort of use is improved. The electrode sheets 7 are connected to the processor 8 through wires.

In an exemplary embodiment, the wearable sleep aid may further include a temperature sensor 11 and a power supply 15. The temperature sensor 11 may be used to sense the ambient temperature, and the output end of the temperature sensor 11 is electrically connected to the input end of the processor 8. The temperature sensor 11 is arranged at a side of the eye mask 5 or U-shaped pillow 6 away from the user. When the ambient temperature detected by the temperature sensor 11 is lower than 20° C., the processor 8 controls the heater 12 to perform heating.

The power supply 15 may include a rechargeable battery, and the output end of the power supply 15 is electrically connected to the power end of the processor 8 and the power end of the signal transmitter 14, for supplying power to the processor 8 and the signal transmitter 14. The power supply 15 may include a charging interface 9. The charging interface 9 may be a USB interface or other charging interface 9. The charging interface 9 may be arranged at a position close to the ear of the eye mask 5. The charging interface 9 may also be arranged at a side of the U-shaped pillow 6 away from the contact with the human body.

The output device may include one or more of a heater 12, a music player 13, a signal transmitter 14 and a display screen 16. The control end of the heater 12 is electrically connected to the output end of the processor 8, and the heater 12 is arranged on a side of the eye mask 5 close to the user. The heater 12 is continuously heated to keep the temperature of the eyes and surrounding areas constant, so as to relieve eye fatigue, promote blood circulation and improve sleep conditions. The heater 12 may be heated by a resistance wire, heated by graphene, or the like. When the wearable sleep aid includes the U-shaped pillow 6, the heater 12 is arranged on a side of the U-shaped pillow 6 close to the user, and the heater 12 keeps the temperature of the neck and surrounding areas constant, so as to relieve neck fatigue, promote blood circulation, and improve sleep conditions.

The signal transmitter 14 is electrically connected to the output end of the processor 8. The signal transmitter 14 may be a wireless signal transceiver. The wireless signal transmission method may be Bluetooth, WiFi, etc. It may also be a wired signal transmission interface, such as a USB interface. The processor 8 may transmit the data acquired by the processor 8 and the processed results (such as sleep state, stress index, fatigue index, etc.) to a terminal device such as a mobile phone or a PC through the signal transmitter 14, for review by the user. The terminal device may also send a control signal to the processor 8 through the signal transmitter 14, so as to control the heater 12 and the music player 13. The control signal may indicate whether to turn on the heating function, heating to be a preset temperature, heating for a preset time, whether to turn on the music play function, the music type, the volume, etc.

The control end of the music player 13 is electrically connected to the output end of the processor 8. The music player 13 realizes the function of playing sleep aid music to help the user fall asleep quickly. The music player 13 may be an earphone or a speaker. It may be set at a position of the eye mask 5 close to the user's ear. The speaker may be arranged in the eye mask 5. An opening is arranged on the eye mask 5, and the sound-emitting part of the speaker is located at the opening. The connection wire of the earphone may be set as a retractable wire. In the case where the wearable sleep aid includes a U-shaped pillow 6, a blind hole 10 may be provided on the U-shaped pillow 6. The earphone may be retracted into the blind hole 10 when not in use, and may be pulled outside of the blind hole 10 when in use.

The input end of the display screen 16 is electrically connected to the output end of the processor 8. The display screen 16 may be arranged on a side of the eye mask 5 or the U-shaped pillow 6 away from the user. The processor 8 may display the acquired data and processed resulting results (such as sleep status, stress index, fatigue index, etc.) through the display screen 16 for review by the user.

In an exemplary embodiment, the sleep aid device may further include a memory. The memory may store the data acquired by the processor 8 and the processed results (such as sleep state, stress index, fatigue index, etc.). The user may check his recent sleep status, stress change trend, fatigue change trend, etc. through a terminal device.

In an example embodiment, a groove is provided on the filler. The signal transmitter 14, the processor 8, the power supply 15, and the memory may be packaged together into an integral circuit module, which is placed in the groove.

Figure 6:
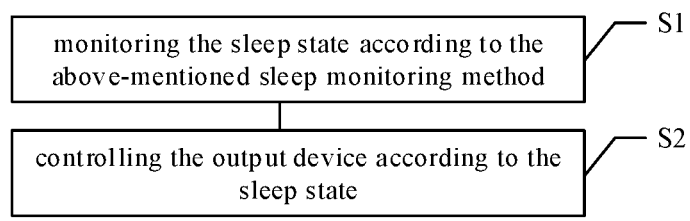
FIG. 6 schematically shows a flowchart of the sleep aid method according to an exemplary implementation of the present invention.

Further, an exemplary embodiment of the present disclosure also provides a sleep aid method, which is applicable to the above-mentioned sleep aid device. Referring to the flowchart of the sleep aid method shown in FIG. 6, the sleep aid method may include the following steps.

In Step S1, the sleep state is monitored according to the above-mentioned sleep monitoring method.

In Step S2, the output device is controlled according to the sleep state.

The sleep monitoring method has been described in detail above, so it will not be repeated here.

In an exemplary embodiment, the step of controlling the output device according to the sleep state may include: when it is detected that the user enters a light sleep period, controlling the volume of the music player 13 to decrease; and when it is detected that the user enters a deep sleep period, controlling the music player 13 to stop playing music, thus creating a sleeping atmosphere for the user to reduce stress and fatigue.

In an example embodiment, the step of controlling the output device according to the sleep state may include: when it is detected that the user enters a light sleep period, controlling the heating temperature of the heater 12 to gradually decrease; and when it is detected that the user enters a deep sleep period, controlling the heater 12 to stop heating, thus creating a sleeping atmosphere for the user to reduce stress and fatigue.

From the description of the above embodiments, those skilled in the art can easily understand that the exemplary embodiments described herein may be implemented by software, or may be implemented by software combined with necessary hardware. Therefore, the technical solutions according to embodiments of the present disclosure may be embodied in the form of a software product. The software product may be stored in a non-volatile storage medium (which may be a CD-ROM, U disk, mobile hard disk, etc.) or on a network, including several instructions to cause a computing device (which may be a personal computer, a server, a mobile terminal, or a network device, etc.) to perform the method according to an embodiment of the present disclosure.

Other embodiments of the present disclosure will readily occur to those skilled in the art upon consideration of the specification and practice of the content disclosed herein. The present application is intended to cover any variations, uses, or adaptations of the present disclosure that follow the general principle of the present disclosure and include common knowledge or techniques in the technical field not disclosed by the present disclosure. The specification and examples are to be regarded as exemplary only, with the true scope and spirit of the disclosure being indicated by the appended claims.

The invention claimed is:

1. A sleep monitoring apparatus, comprising:
a signal acquisition sub-circuit configured to acquire an electroencephalogram (EEG) signal of a user;
a first processing sub-circuit configured to process the EEG signal by at least one of wavelet packet decomposition, wavelet transform, or Fourier transform to obtain energy values of the EEG signal in a plurality of set frequency bands;
a second processing sub-circuit configured to calculate relative energy values of the EEG signal in the plurality of set frequency bands; and
a state determination sub-circuit configured to determine sleep state, mental stress, and fatigue level according to the relative energy values,
wherein the plurality of set frequency bands comprises a first frequency band, a second frequency band, a third frequency band, and a fourth frequency band; and
the first frequency band is greater than or equal to 0.5 Hz and less than 4 Hz, the second frequency band is greater than or equal to 4 Hz and less than 8 Hz, the third frequency band is greater than or equal to 8 Hz and less than 12 Hz, and the fourth frequency band is greater than or equal to 12 Hz and less than or equal to 30 Hz,
wherein the second processing sub-circuit is further configured to:
calculate a sum of the energy values of the EEG signal; and
determine each of the relative energy values as a ratio of the energy value of the EEG signal in a respective set frequency band to the sum,
wherein the state determination sub-circuit is further configured to:
calculate a sleep index SI by formulas of:

$$SI=(K1*E1+K2*E2)/(K3*E3+K4*E4),$$

$$K1+K2=1, \text{ and}$$

$$K3+K4=1,$$

where, K1 has a value range of 0.3-0.5, K3 has a value range of 0.7-1, E1 is the relative energy value of the EEG signal in the first frequency band, E2 is the relative energy value of the EEG signal in the second frequency band, E3 is the relative energy value of the EEG signal in the third frequency band, and E4 is the relative energy value of the EEG signal in the fourth frequency band; and
calculate a deep sleep index DI by a formula of:

$$DI=E1/E2,$$

wherein, if SI<TH1, it is determined to be an awake period;
if SI>TH1 and DI<TH2, it is determined to be a light sleep period; and if SI>TH1 and DI>TH2, it is determined to be a deep sleep period, and
wherein, TH1 is a constant having a value range of 1.5-4, and TH2 is a constant having a value range of 0.8-2; and
an output device,
wherein the output device comprises at least one of a heater and a music player electrically connected to the state determination sub-circuit and is configured to operate according to a control signal output by the state determination sub-circuit indicative of the sleep state.

2. A sleep monitoring method, comprising:
acquiring an electroencephalogram (EEG) signal from a user;
processing the EEG signal by at least one of wavelet packet decomposition, wavelet transform, or Fourier transform to obtain energy values of the EEG signal in a plurality of set frequency bands;
calculating relative energy values of the EEG signal in the plurality of set frequency bands; and
determining sleep state, mental stress, and fatigue level according to the relative energy values,
wherein the plurality of set frequency bands comprises a first frequency band, a second frequency band, a third frequency band, and a fourth frequency band; and
the first frequency band is greater than or equal to 0.5 Hz and less than 4 Hz, the second frequency band is greater than or equal to 4 Hz and less than 8 Hz, the third frequency band is greater than or equal to 8 Hz and less than 12 Hz, and the fourth frequency band is greater than or equal to 12 Hz and less than or equal to 30 Hz,
wherein the calculating the relative energy values of the EEG signal in the plurality of set frequency bands comprises:
calculating a sum of the energy values of the EEG signal; and
determining each of the relative energy values as a ratio of the energy value of the EEG signal in a respective set frequency band to the sum,
wherein the determining the sleep state according to the relative energy values comprises:
calculating a sleep index SI by formulas of:

$$SI=(K1*E1+K2*E2)/(K3*E3+K4*E4),$$

$$K1+K2=1, \text{ and}$$

$$K3+K4=1,$$

where, K1 has a value range of 0.3-0.5, K3 has a value range of 0.7-1, E1 is the relative energy value of the EEG signal in the first frequency band, E2 is the relative energy value of the EEG signal in the second frequency band, E3 is the relative energy value of the EEG signal in the third frequency band, and E4 is the relative energy value of the EEG signal in the fourth frequency band; and
calculating a deep sleep index DI by a formula of:

$$DI=E1/E2,$$

wherein, if SI<TH1, it is determined to be an awake period; if SI>TH1 and DI<TH2, it is determined to be a light sleep period; and if SI>TH1 and DI>TH2, it is determined to be a deep sleep period,
and wherein, TH1 is a constant having a value range of 1.5-4, and TH2 is a constant having a value range of 0.8-2; and
outputting a control signal indicative of the sleep state to an output device,
wherein the output device comprises at least one of a heater and a music player and operates according to the control signal.

3. The sleep monitoring method according to claim 2, wherein the determining the mental stress according to the relative energy values comprises: calculating a pressure index S according to a formula of:

$$S=E2/(E3+E4),$$

wherein the larger the stress index, the higher the mental stress.

4. The sleep monitoring method according to claim 2, wherein the determining the fatigue degree according to the relative energy values comprises: calculating a fatigue index F according to a formula of $$F=(E1+E2)/E4,$$

wherein the larger the fatigue index, the deeper the fatigue degree.

5. A sleep aid device, comprising:
a wearable sleep aid;
an electrode sheet arranged on the wearable sleep aid and configured to be attached to a head of a user;
a processor electrically connected to the electrode sheet, and configured to receive the EEG signal acquired by the electrode sheet, thereby implementing the sleep monitoring method according to claim 2, and output a control signal indicative of the sleep state; and
an output device,
wherein the output device comprises at least one of a heater and a music player electrically connected to the processor and is configured to operate according to the control signal output by the processor.

6. The sleep aid device according to claim 5, wherein the wearable sleep aid comprises one or both of an eye mask and a U-shaped pillow.

7. The sleep aid device according to claim 5, wherein the wearable sleep aid further comprises: a temperature sensor, electrically connected to an input end of the processor, and configured to detect an ambient temperature.

8. The sleep aid device according to claim 5, wherein:
the output device further comprises one or more of a signal transmitter and a display screen;
a control end of the heater is electrically connected to an output end of the processor;
a control end of the music player is electrically connected to the output end of the processor;
the signal transmitter is electrically connected to the output end of the processor;
and an input end of the display screen is electrically connected to the output end of the processor.

9. The sleep aid device according to claim 8, wherein the music player is an earphone or a speaker.

10. The sleep aid device according to claim 9, wherein the earphone comprises a retractable connection wire.

11. A sleep aid method, applicable to the sleep aid device according to claim 5, wherein the sleep aid method comprises:
monitoring the sleep state by a sleep monitoring method; and controlling the output device according to the sleep state,
wherein the output device comprises at least one of a heater and a music player; and
wherein the sleep monitoring method comprises:
acquiring an electroencephalogram (EEG) signal from a user;
processing the EEG signal by at least one of wavelet packet decomposition, wavelet transform, or Fourier transform to obtain energy values of the EEG signal in a plurality of set frequency bands;
calculating relative energy values of the EEG signal in the plurality of set frequency bands; and
determining sleep state, mental stress, and fatigue level according to the relative energy values,
wherein the plurality of set frequency bands comprises a first frequency band, a second frequency band, a third frequency band, and a fourth frequency band; and the first frequency band is greater than or equal to 0.5 Hz and less than 4 Hz, the second frequency band is greater than or equal to 4 Hz and less than 8 Hz, the third frequency band is greater than or equal to 8 Hz and less than 12 Hz, and the fourth frequency band is greater than or equal to 12 Hz and less than or equal to 30 Hz, wherein the calculating the relative energy values of the EEG signal in the plurality of set frequency bands comprises:

calculating a sum of the energy values of the EEG signal; and determining each of the relative energy values as a ratio of the energy value of the EEG signal in a respective set frequency band to the sum, wherein the determining the sleep state according to the relative energy values comprises:

calculating a sleep index SI by formulas of:

$$SI=(K1*E1+K2*E2)/(K3*E3+K4*E4),$$

$$K1+K2=1, \text{ and}$$

$$K3+K4=1,$$

where, K1 has a value range of 0.3-0.5, K3 has a value range of 0.7-1, E1 is the relative energy value of the EEG signal in the first frequency band, E2 is the relative energy value of the EEG signal in the second frequency band, E3 is the relative energy value of the EEG signal in the third frequency band, and E4 is the relative energy value of the EEG signal in the fourth frequency band; and calculating a deep sleep index DI by a formula of:

$$DI=E1/E2,$$

wherein, if SI<TH1, it is determined to be an awake period; if SI>TH1 and DI<TH2, it is determined to be a light sleep period; and if SI>TH1 and DI>TH2, it is determined to be a deep sleep period, and wherein, TH1 is a constant having a value range of 1.5-4, and TH2 is a constant having a value range of 0.8-2; and outputting a control signal indicative of the sleep state to the output device and controlling the output device according to the control signal.

12. The sleep aid method according to claim 11, wherein the controlling the output device according to the sleep state comprises:

in response that the user is detected to enter a light sleep period, controlling the music player to decrease in volume; and in response that the user is detected to enter a deep sleep period, controlling the music player to stop playing music.

13. The sleep aid method according to claim 11, wherein the controlling the output device according to the sleep state comprises:

in response that the user is detected to enter a light sleep period, controlling the heater to gradually decrease in heating temperature; and in response that the user is detected to enter a deep sleep period, controlling the heater to stop heating.

14. The sleep aid method according to claim 11, wherein the wearable sleep aid comprises one or both of an eye mask and a U-shaped pillow.

15. The sleep aid method according to claim 11, wherein the wearable sleep aid further comprises a temperature sensor electrically connected to an input end of the processor, and configured to detect an ambient temperature.

16. The sleep aid method according to claim 11, wherein:

the output device further comprises one or more of a signal transmitter and a display screen;

a control end of the heater is electrically connected to an output end of the processor;

a control end of the music player is electrically connected to the output end of the processor;

the signal transmitter is electrically connected to the output end of the processor; and an input end of the display screen is electrically connected to the output end of the processor.

17. The sleep aid method according to claim 16, wherein the music player is an earphone or a speaker.

* * * * *